(12) United States Patent
Okusu et al.

(10) Patent No.: US 9,318,079 B2
(45) Date of Patent: Apr. 19, 2016

(54) MOBILE TERMINAL APPARATUS WITH DISPLAY UNIT

(71) Applicant: FUJIFILM Corporation, Tokyo (JP)

(72) Inventors: Kiyohisa Okusu, Tokyo (JP); Satoshi Ueda, Tokyo (JP); Yuya Kudo, Tokyo (JP); Hironori Matsumasa, Tokyo (JP); Yasunori Ohta, Ashigarakami (JP)

(73) Assignee: FUJIFILM CORPORATION, Tokyo (JP)

( * ) Notice: Subject to any disclaimer, the term of this patent is extended or adjusted under 35 U.S.C. 154(b) by 79 days.

(21) Appl. No.: 14/191,184

(22) Filed: Feb. 26, 2014

(65) Prior Publication Data

US 2014/0285525 A1    Sep. 25, 2014

(30) Foreign Application Priority Data

Mar. 25, 2013    (JP) ................. 2013-061885

(51) Int. Cl.
| | |
|---|---|
| G09G 5/38 | (2006.01) |
| G06F 17/30 | (2006.01) |
| A61B 6/00 | (2006.01) |
| G06F 3/0488 | (2013.01) |
| G06F 1/16 | (2006.01) |
| G06F 3/01 | (2006.01) |
| G06F 3/0346 | (2013.01) |
| G06F 19/00 | (2011.01) |

(52) U.S. Cl.
CPC ............. G09G 5/38 (2013.01); A61B 6/461 (2013.01); A61B 6/467 (2013.01); G06F 1/1694 (2013.01); G06F 3/017 (2013.01); G06F 3/0346 (2013.01); G06F 3/0488 (2013.01); G06F 17/30067 (2013.01); G06F 17/30274 (2013.01); G06F 19/321 (2013.01); G06F 19/3406 (2013.01); G06F 19/3418 (2013.01)

(58) Field of Classification Search
None
See application file for complete search history.

(56) References Cited

U.S. PATENT DOCUMENTS

| | | | |
|---|---|---|---|
| 2005/0251036 A1* | 11/2005 | Abuhamad | 600/437 |
| 2007/0237377 A1* | 10/2007 | Oosawa | 382/128 |
| 2009/0257550 A1* | 10/2009 | Moriya | 378/4 |

(Continued)

FOREIGN PATENT DOCUMENTS

| | | |
|---|---|---|
| JP | 2011-92687 A | 5/2011 |
| JP | 2011-191515 A | 9/2011 |
| JP | 2011-205236 A | 10/2011 |

OTHER PUBLICATIONS

European Search Report dated Aug. 5, 2014.

*Primary Examiner* — Mark Zimmerman
*Assistant Examiner* — Michelle Chin
(74) *Attorney, Agent, or Firm* — McGinn IP Law Group PLLC

(57) ABSTRACT

In a mobile terminal apparatus, a display unit displays a diagnostic image read from an image storage device. The image storage device stores plural image groups, each of which includes plural diagnostic images. Movement of the display unit is detected. Assuming that the display unit is moved in a mode of transverse movement while a first diagnostic image included in a first image group is displayed on the display unit, then changeover is carried out to display a second diagnostic image being included in the first image group and different from the first diagnostic image. Assuming that the display unit is moved in a mode of a single shake different from the mode of transverse movement while the first diagnostic image is displayed on the display unit, then changeover is carried out to display a third diagnostic image being included in an image group different from the first image group.

22 Claims, 9 Drawing Sheets

(56) References Cited

U.S. PATENT DOCUMENTS

2011/0074813 A1 3/2011 Masumoto
2012/0120000 A1 5/2012 Lucic et al.
2013/0002718 A1 1/2013 Kato

* cited by examiner

F I G . 10
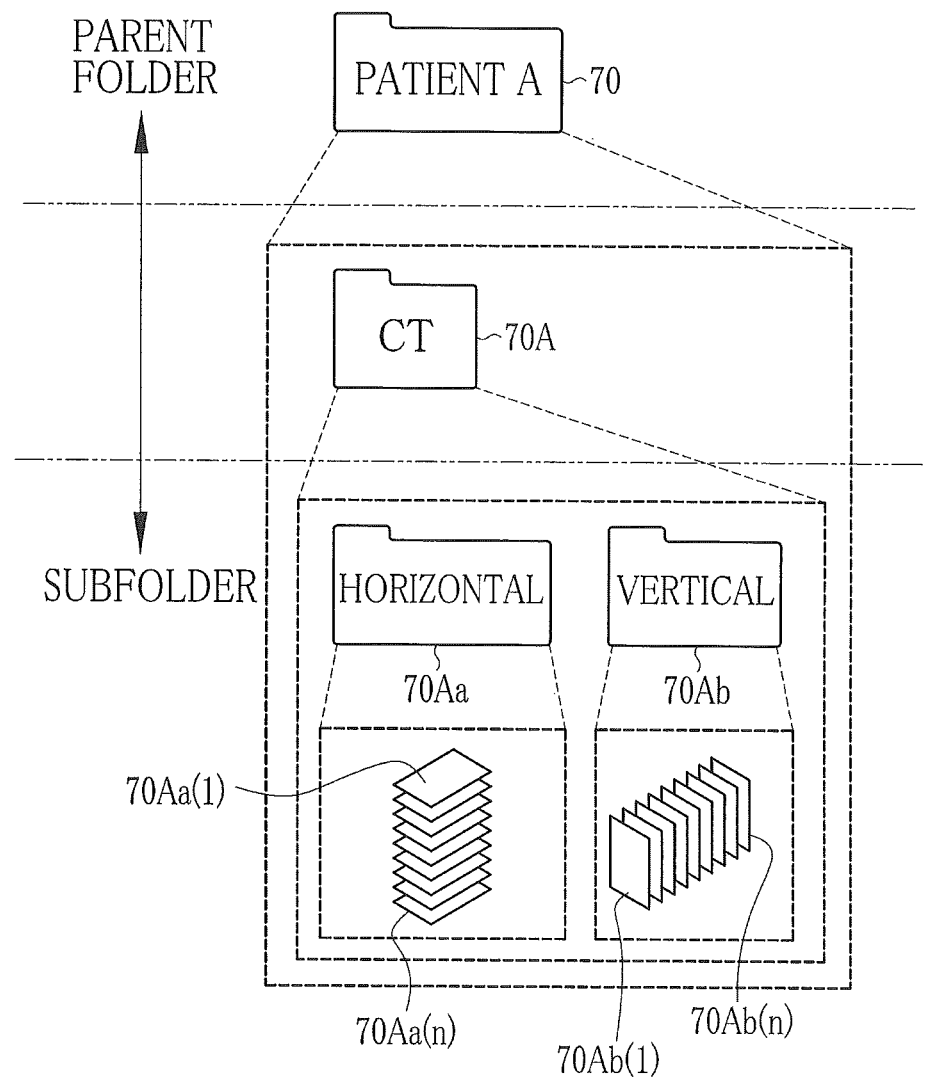

MOBILE TERMINAL APPARATUS WITH DISPLAY UNIT

BACKGROUND OF THE INVENTION

1. Field of the Invention

The present invention relates to a mobile terminal apparatus with a display unit. More particularly, the present invention relates to a mobile terminal apparatus in which a diagnostic image can be viewed easily with a display unit and diagnosis can be smoothly performed.

2. Description Related to the Prior Art

Diagnostic images are widely utilized in a medical field, for example, CT images or other sectional images. The diagnostic images are grouped in plural groups or series according to their relevancy, and stored in image folders as image groups. A doctor or operator views the diagnostic images by the unit of each of the image groups. A plurality of image groups (image folders) are provided in consideration of plural image dates of imaging or examination. The diagnostic images can be compared with one another between the image groups for the purpose of diagnosis.

U.S. Pat. Pub. No. 2011/074,813 (corresponding to JP-A 2011-092687) discloses a display control method in which a control window is displayed beside the diagnostic image, and a tag, slider and the like are indicated in the control window. A mouse, keyboard or other input devices are manipulated to operate the tag or slider, to change over the diagnostic image displayed in a common image group, or to change over the diagnostic image between two or more of the image groups.

Also, JP-A 2011-205236 and U.S. Pat. Pub. No. 2013/002,718 (corresponding to JP-A 2011-191515) disclose a display control method in which content information or menu in the display is changed over according to motion of a mobile terminal apparatus, for example, a shake and rotation.

Today, the use of the mobile terminal apparatus for medical purposes is widespread. The diagnostic image is displayed by the mobile terminal apparatus for a doctor to diagnose the mobile terminal apparatus remotely even while he or she is located outside a hospital facility. However, a display panel of the mobile terminal apparatus is small. Assuming that the control window of U.S. Pat. Pub. No. 2011/074,813 is displayed for display changeover of the diagnostic image or other manipulation, a display area for the diagnostic image becomes considerably small to make it difficult to view the diagnostic image.

It is conceivable to change over the diagnostic image according to the motion of the mobile terminal apparatus as suggested in JP-A 2011-205236 and U.S. Pat. Pub. No. 2013/002,718. However, two display changeover operations are used together for the diagnosis, including that of the diagnostic image within the image group and that of the diagnostic image between the image groups. However, it is impossible according to those documents to use the two display changeover operations together. Diagnosis cannot be carried out smoothly.

SUMMARY OF THE INVENTION

In view of the foregoing problems, an object of the present invention is to provide a mobile terminal apparatus in which a diagnostic image can be viewed easily with a display unit and diagnosis can be smoothly performed.

In order to achieve the above and other objects and advantages of this invention, a mobile terminal apparatus includes an image storage device for storing at least first and second image groups, each of the first and second image groups including a plurality of diagnostic images. A display unit displays one of the diagnostic images read from the image storage device. An orientation sensor detects first and second motion modes of the display unit with a difference in movement from one another. There is a display control unit for display control of the display unit by sending an image signal thereto, and for changing over the image signal according to an output of the orientation sensor, wherein assuming that the display unit is moved in the first motion mode while a first diagnostic image included in the first image group is displayed on the display unit, then the display control unit carries out changeover to display a second diagnostic image being included in the first image group and different from the first diagnostic image, and assuming that the display unit is moved in the second motion mode while the first diagnostic image is displayed on the display unit, then the display control unit carries out changeover to display a third diagnostic image included in the second image group.

Preferably, furthermore, a terminal housing contains the display unit.

Preferably, furthermore, there is a communication interface for connection to a server apparatus by communication network connection. A controller acquires the diagnostic images from the server apparatus through the communication interface, and stores the diagnostic images to the image storage device.

Preferably, the first motion mode is to move the display unit linearly.

Preferably, each of the image groups is defined by arranging the diagnostic images in a predetermined sequence. While the display unit is moved linearly in a thickness direction, the diagnostic images are serially changed over according to the sequence to be displayed on the display unit at each time of linear movement in the thickness direction at a predetermined amount.

In a preferred embodiment, the second motion mode is to shake the display unit.

Preferably, the second motion mode is to shake the display unit two times.

In another preferred embodiment, the second motion mode is to move the display unit rotationally between a horizontal orientation in which a display surface is horizontally extended and a vertical orientation in which the display surface is vertically extended.

Preferably, the first image group has diagnostic images for display in the horizontal orientation, and the second image group has diagnostic images for display in the vertical orientation. The display control unit causes the display unit to display one of the diagnostic images of the first image group in a case of the horizontal orientation, and to display one of the diagnostic images of the second image group in a case of the vertical orientation.

Preferably, the second motion mode is to rotate the display unit about an axis extending vertically in a vertical orientation in which a display surface of the display unit is vertically extended.

Preferably, the first image group has a sagittal slice image for the diagnostic images, and the second image group has a coronal slice image for the diagnostic images. The vertical orientation is constituted by a first vertical orientation extending along a sagittal plane, and a second vertical orientation extending along a coronal plane being perpendicular to a horizontal surface and the sagittal plane. The display control unit causes the display unit to display the sagittal slice image of the first image group in a case of the first vertical orientation, and to display the coronal slice image of the second image group in a case of the second vertical orientation.

In another preferred embodiment, the image storage device stores plural data groups of a higher level, each of the data groups having the first and second image groups. Assuming that the display unit is moved in a third motion mode different from the first and second motion modes while the first diagnostic image is displayed on the display unit, then the display control unit carries out changeover to display a fourth diagnostic image included in one of the data groups different from a data group of the first diagnostic image.

Preferably, assuming that the display unit is moved in the third motion mode while the first diagnostic image is displayed on the display unit, then the display control unit outputs message information to the display unit for possibility of changeover. Furthermore, an input interface, externally operable, inputs a signal for allowing the changeover to the fourth diagnostic image, to change over the display unit with the display control unit.

Preferably, a subject body in the diagnostic image is different between the plural data groups.

Preferably, the diagnostic images are a sectional image of a subject body, and each of the first and second image groups is formed at one time of imaging of the subject body.

Preferably, the sectional image is a CT or MRI image.

Preferably, the first image group includes diagnostic images of a first imaging modality, and the second image group includes diagnostic images of a second imaging modality different from the first imaging modality.

In still another preferred embodiment, the first image group includes diagnostic images with first image date information, and the second image group includes diagnostic images with second image date information different from the first image date information.

Preferably, the image storage device stores first and second directories adapted to store diagnostic images of imaging modalities different from one another. First and second subdirectories are located in at least one of the first and second directories, for storing diagnostic images with image date information different from one another. The first image group is the first directory or the first subdirectory, and the second image group is the second directory or the second subdirectory.

Preferably, a display method is provided, and includes a step of displaying a diagnostic image read from an image storage device on a display unit. The image storage device stores a plurality of image groups, each of the image groups including a plurality of diagnostic images. Movement of the display unit is detected. Assuming that the display unit is moved in a first motion mode while a first diagnostic image included in a first image group is displayed on the display unit, then changeover is carried out to display a second diagnostic image being included in the first image group and different from the first diagnostic image. Assuming that the display unit is moved in a second motion mode different from the first motion mode while the first diagnostic image is displayed on the display unit, then changeover is carried out to display a third diagnostic image being included in an image group different from the first image group.

Preferably, a computer-executable program for display is provided, and includes a program code for displaying a diagnostic image read from an image storage device on a display unit. The image storage device stores a plurality of image groups, each of the image groups including a plurality of diagnostic images. A program code is for detecting movement of the display unit. A program code is for, assuming that the display unit is moved in a first motion mode while a first diagnostic image included in a first image group is displayed on the display unit, carrying out changeover to display a second diagnostic image being included in the first image group and different from the first diagnostic image. A program code is for, assuming that the display unit is moved in a second motion mode different from the first motion mode while the first diagnostic image is displayed on the display unit, carrying out changeover to display a third diagnostic image being included in an image group different from the first image group.

Consequently, it is possible to view a diagnostic image easily with a display unit and to perform the diagnosis smoothly, because two motion modes of the display unit are utilized readily to change over the display image in a clarified manner.

BRIEF DESCRIPTION OF THE DRAWINGS

The above objects and advantages of the present invention will become more apparent from the following detailed description when read in connection with the accompanying drawings, in which:

FIG. 10 is an explanatory view illustrating a hierarchical tree structure for storing the diagnostic images;

DETAILED DESCRIPTION OF THE PREFERRED EMBODIMENT(S) OF THE PRESENT INVENTION

Figure 1:
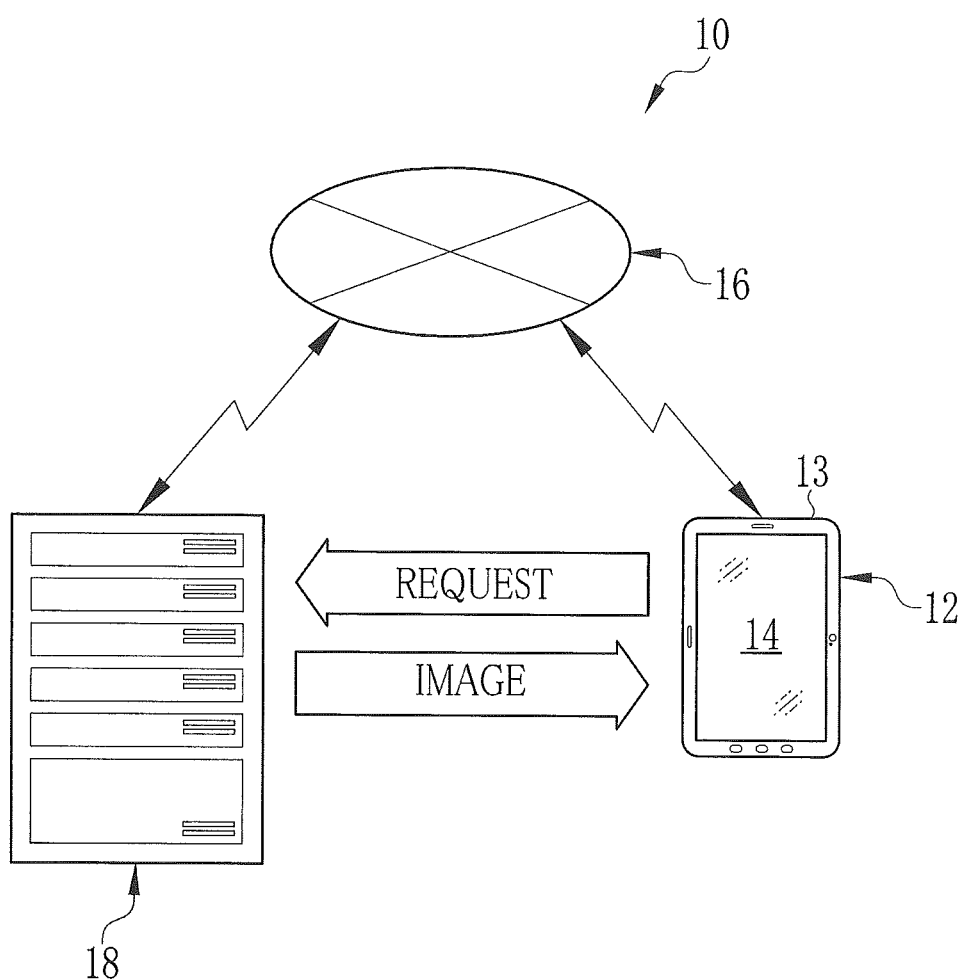
FIG. 1 is a block diagram schematically illustrating an image viewing system.

In FIG. 1, an image viewing system 10 or remote diagnostic system (medical support system) includes a mobile terminal apparatus 12. The mobile terminal apparatus 12 includes a terminal housing 13, and a display unit 14 or display panel fitted in the terminal housing 13. A server apparatus 18 or image server is connected to the mobile terminal apparatus 12 by a communication network 16, for example, the Internet or local area network (LAN). The server apparatus 18 stores diagnostic images formed by medical imaging in a hospital facility or other medical service provider. The mobile terminal apparatus 12 accesses the server apparatus 18 and downloads the diagnostic images from the server apparatus 18. The display unit 14 is driven to display the downloaded diagnostic images.

Figure 2:
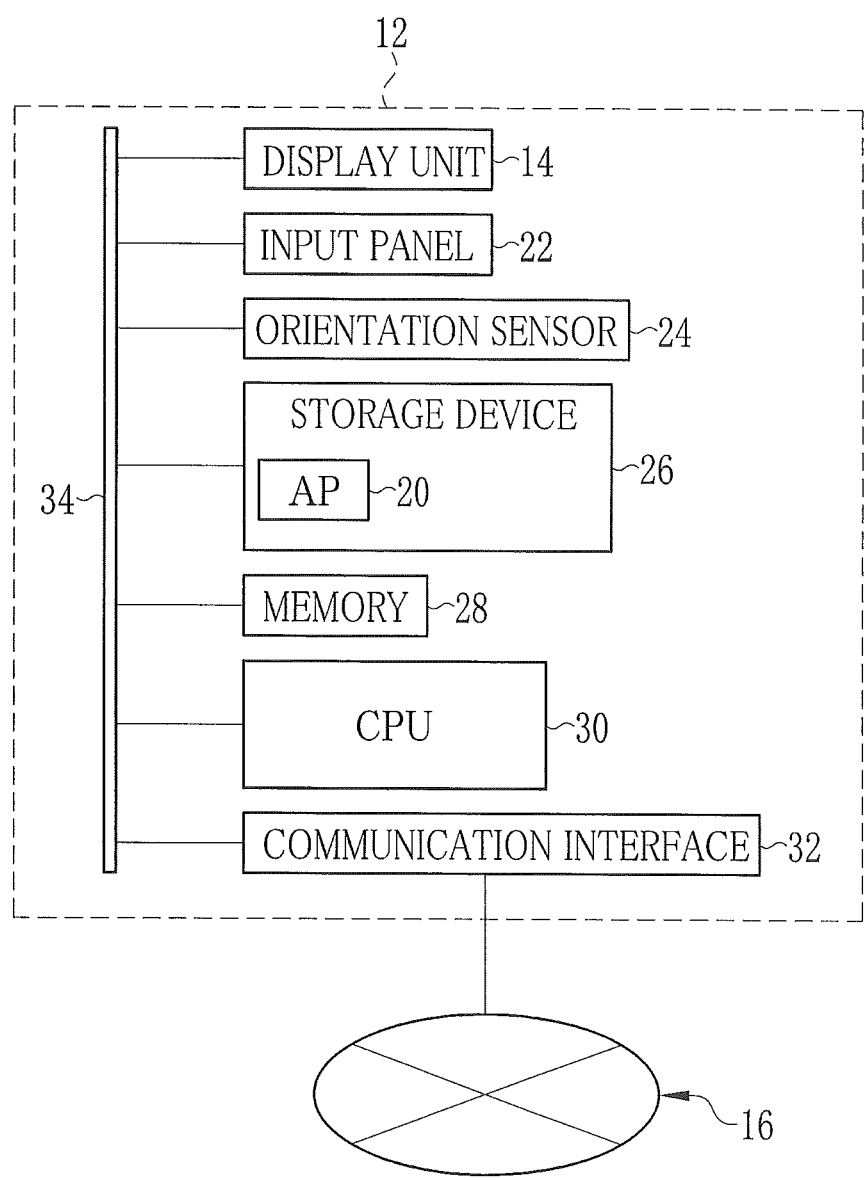
FIG. 2 is a block diagram schematically illustrating a mobile terminal apparatus.

In FIG. 2, various computer-executable programs are installed in a portable computer to constitute the mobile terminal apparatus 12. Examples of the portable computer include a tablet type, notebook type and the like. Examples of the programs include an application program 20 (AP) for functioning as a portable display apparatus, a control program such as an operating system (OS), and the like.

In addition to the display unit 14, the mobile terminal apparatus 12 includes an input panel 22, an orientation sensor 24, a storage device 26, a memory 28, a CPU 30 (controller) and a communication interface 32, which are interconnected by a data bus 34. The input panel 22 is a combination of plural control buttons, the display unit 14, and sensors of a touch panel structure. In case a user sets inputs in the mobile terminal apparatus 12, the input panel 22 detects the inputs.

Examples of the orientation sensor 24 area gyro sensor, an acceleration sensor, a magnetic sensor for detecting the geomagnetic field, and a combination of two or more of those sensors. The orientation sensor 24 detects one of the horizontal and vertical orientations of the portable display unit 12, and a direction and amount of movement of the mobile terminal apparatus 12.

In the present embodiment, the orientation sensor 24 detects a plurality of motion modes, for example, a transverse movement (slide), a single shake and a double shake. In the transverse movement, the mobile terminal apparatus 12 is transversely moved in one of forward and backward directions (as a thickness direction in linear movement) with reference to the display unit 14. The orientation sensor 24 also detects an amount of shift in the motion mode of the transverse movement. In the single shake, the mobile terminal apparatus 12 is shaken up and down for one time. In the double shake, the mobile terminal apparatus 12 is shaken up and down for two times.

The storage device 26 is such a storage medium as solid-state drive (SSD) or hard disk, and stores the control program. The memory 28 is a working memory with which the CPU 30 performs tasks. The CPU 30 controls various elements in the computer by performing the control according to the control program after loading the memory 28 with the control program. The communication interface 32 is a network interface for communication control with the communication network 16. The mobile terminal apparatus 12 communicates with the server apparatus 18 by use of the communication interface 32.

The application program 20 stored in the storage device 26 is a display software for display control of diagnostic images. The application program 20 includes program code for downloading a diagnostic image by accessing the server apparatus 18, program code for driving the display unit 14 to display the diagnostic image downloaded from the server apparatus 18, and program code for changing over the diagnostic image in the display unit 14 according to a motion mode of the mobile terminal apparatus 12. The CPU 30 loads the memory 28 with the display software, and controls various elements of the computer by processing according to the display software.

Figure 3:
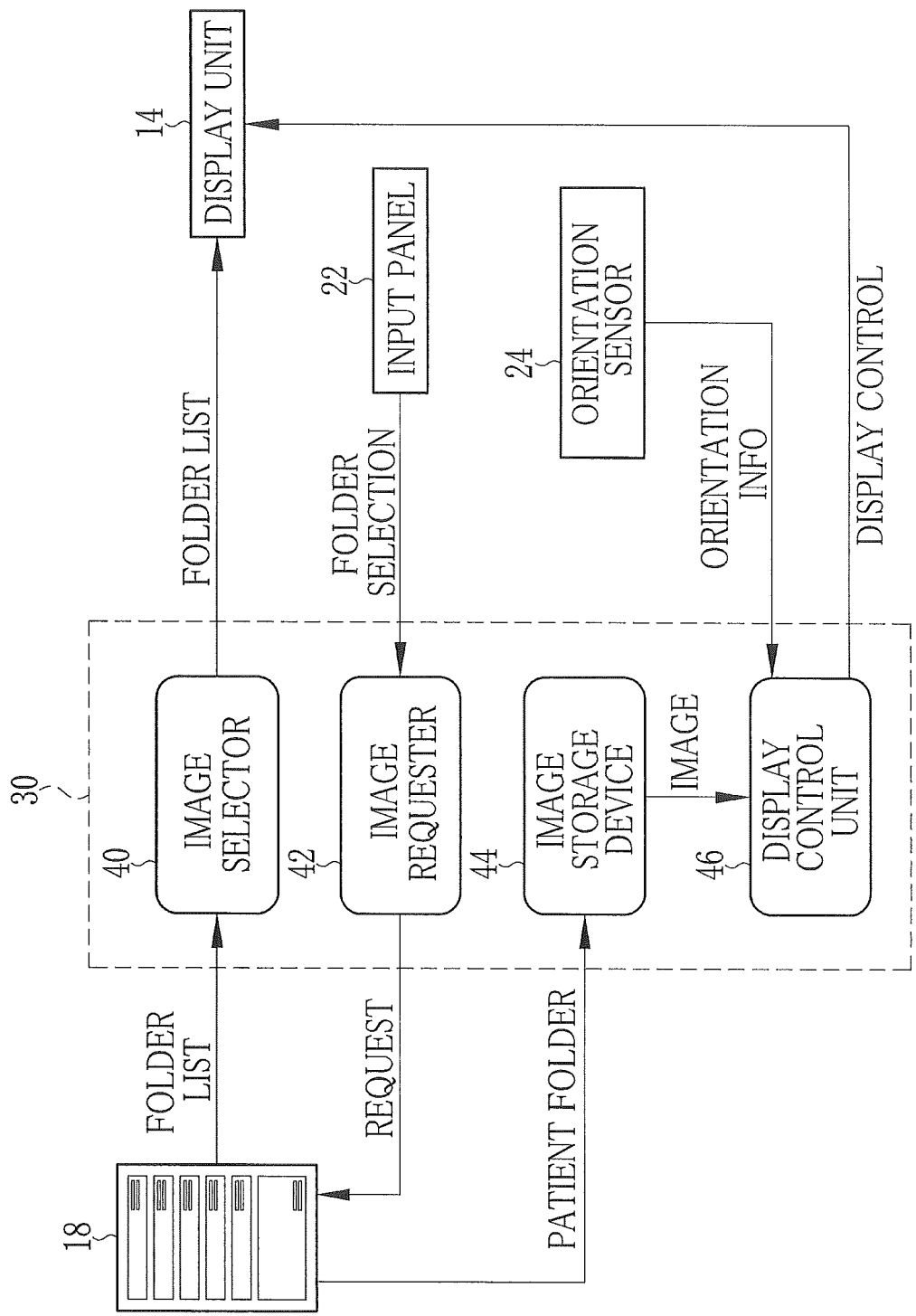
FIG. 3 is a block diagram schematically illustrating a CPU.

In FIG. 3, the CPU 30 operates by running the display software with the memory 28, and comes to include an image selector 40, an image requester 42, an image storage device 44 and a display control unit 46.

The image selector 40 is operated by startup of the display software, and selects diagnostic images to be downloaded from the server apparatus 18 to the mobile terminal apparatus 12. Plural folders are provided in the server apparatus 18, for example, folders with names of patients. Each of the folders stores diagnostic images of the patient in association with the folder. The image selector 40 accesses the server apparatus 18, acquires a list of the patients (folder names), and causes the display unit 14 to display the list. A user or operator manipulates the input panel 22, and designates one of the names displayed on the display unit 14 to select a folder for downloading.

Upon selecting the folder, the image requester 42 is driven to transmit a request for the folder to the server apparatus 18. The server apparatus 18 upon receiving the request transmits or distributes the folder to the mobile terminal apparatus 12. For any of the images, diagnostic images are downloaded to the mobile terminal apparatus 12 by a unit of the folder of each of the patients. The patient folder downloaded from the server apparatus 18 is stored to the image storage device 44.

Plural folders of lower tree levels are stored in a patient folder downloaded from the server apparatus 18, and are grouped according to predetermined conditions. Also, plural subfolders are stored in the folders. A set of plural diagnostic images with relevancy to one another are stored in the subfolder at a lowest tree level. See FIG. 6.

Figure 4:
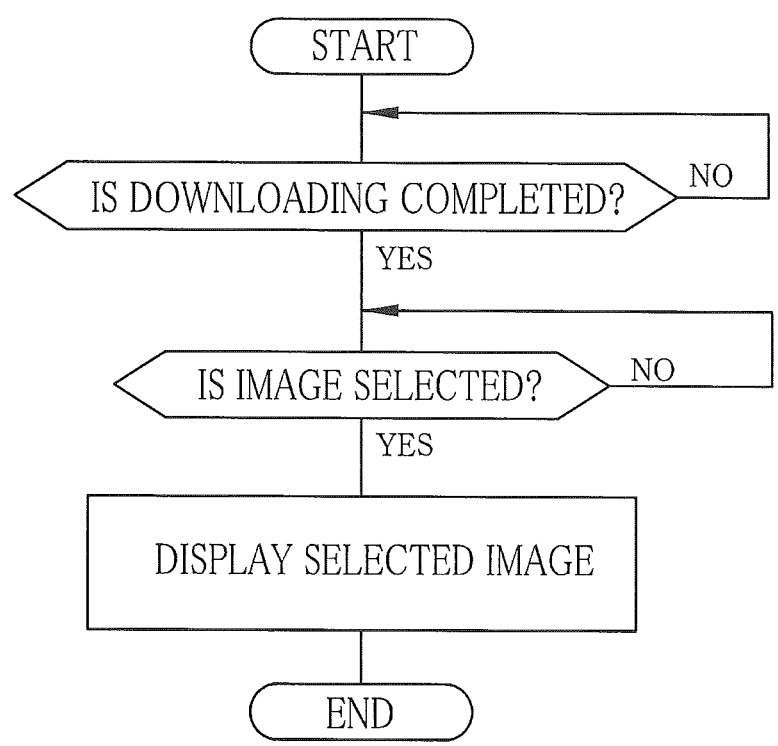
FIG. 4 is a flow chart illustrating display of a diagnostic image.

In FIG. 4, the display control unit 46 selects diagnostic images among those stored in a downloaded patient folder of each one of the patients upon completion of downloading diagnostic images, and drives the display unit 14 to display the selected diagnostic images. The display control unit 46 causes the display unit 14 to display a selection menu for designating the folders from the highest tree level to the lowest. A user or doctor designates the folders sequentially from the highest according to the selection menu. Then the display control unit 46 causes the display unit 14 to display a first one of diagnostic images from the subfolder as an initial diagnostic image upon designating the subfolder at the lowest tree level.

Figure 5:
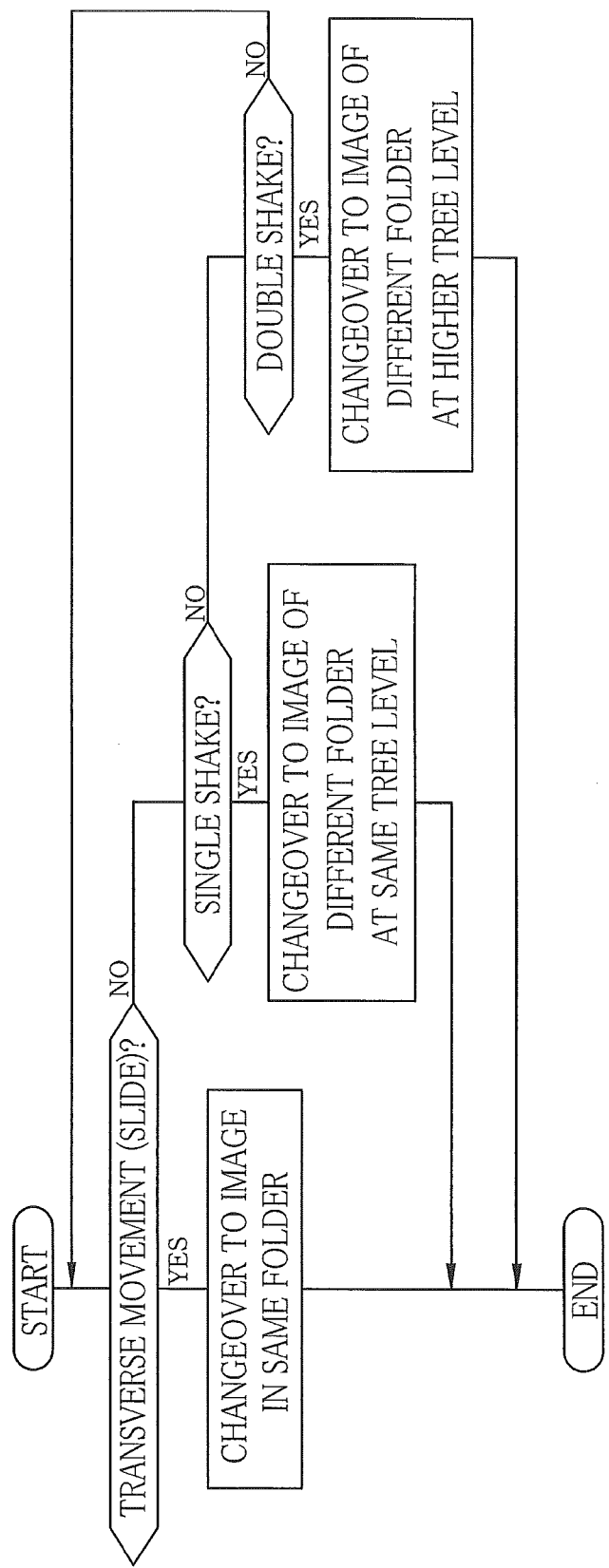
FIG. 5 is a block diagram illustrating changeover of the diagnostic image.

The display control unit 46 after displaying an initial image, operates according to a signal from the orientation sensor 24 as illustrated in FIG. 5. The display control unit 46 monitors occurrence of a transverse movement of the mobile terminal apparatus 12 in the forward or backward direction (first motion mode), occurrence of a single shake of the mobile terminal apparatus 12 (second motion mode), and occurrence of a double shake of the mobile terminal apparatus 12 (third motion mode).

Then the display control unit 46 changes over the display unit 14 from the first diagnostic image to a second diagnostic image which is stored in the same folder as the first diagnostic image but different from the first diagnostic image, in response to transverse movement of the mobile terminal apparatus 12 in a forward or backward direction. See FIG. 7.

Figure 8:
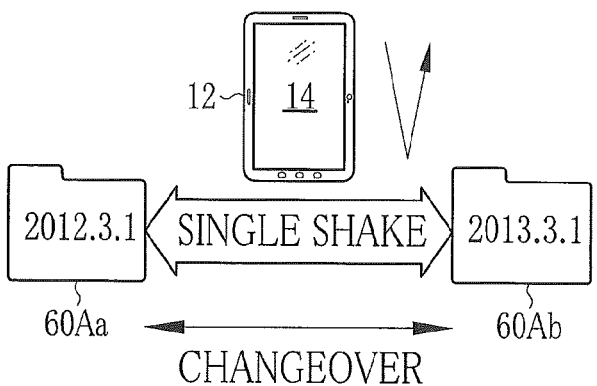
FIG. 8 is an explanatory view illustrating changeover of diagnostic images between plural folders upon a single shake.

In case the mobile terminal apparatus 12 is shaken with a single shake, then the display control unit 46 displays a second diagnostic image on the display unit 14 in place of the display image as illustrated in FIG. 8, the second diagnostic image being stored in a folder at the same tree level as the display image and different from the folder of the display image.

Figure 9:
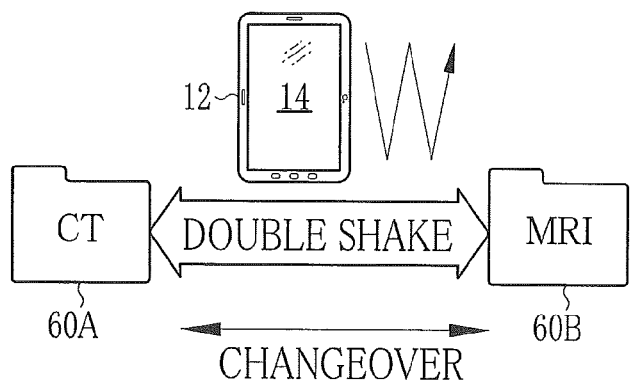
FIG. 9 is an explanatory view illustrating changeover of diagnostic images between plural folders of different tree levels upon a double shake.

In case the mobile terminal apparatus 12 is shaken with a double shake, then the display control unit 46 displays a second diagnostic image on the display unit 14 in place of the display image as illustrated in FIG. 9, the second diagnostic image being stored in a parent folder at a higher tree level than a folder of the display image by one level and different from the folder of the display image.

Figure 6:
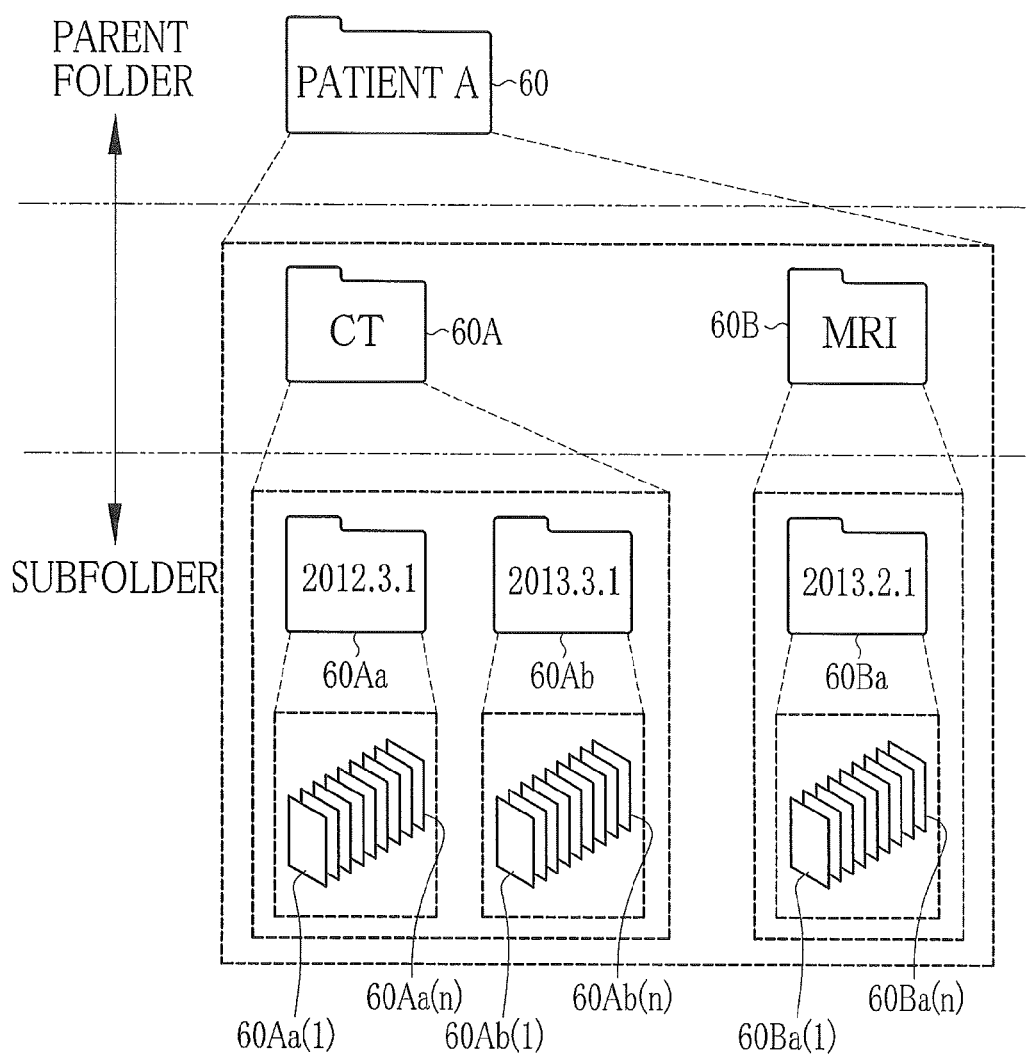
FIG. 6 is an explanatory view illustrating a hierarchical tree structure for storing diagnostic images.

The display control of the display control unit 46 for diagnostic images is described hereinafter in detail. In FIG. 6, a patient folder 60 of a patient A as a parent directory (data group) is downloaded from the server apparatus 18. The display unit 14 displays diagnostic images originally stored in the patient folder 60, namely, diagnostic images 60Aa(1)-(n), 60Ab(1)-(n) and 60Ba(1)-(n).

In FIG. 6, the patient folder 60 of the patient A contains a CT imaging folder 60A and an MRI imaging folder GOB as directories. The CT imaging folder 60A contains a first date folder 60Aa as a subfolder or image group (subdirectory) of an image date of 1 Mar. 2012, and a second date folder 60Ab as a subfolder or image group (subdirectory) of an image date of 1 Mar. 2013. The first and second date folders 60Aa and 60Ab contain the diagnostic images 60Aa(1)-(n) and 60Ab(1)-(n) as sequences of CT images from the head to the legs. The MRI imaging folder 60B contains a third date folder 60Ba as a subfolder or image group (subdirectory) of an image date of 1 Feb. 2013. The third date folder 60Ba contains the diagnostic images 60Ba(1)-(n) as a sequence of MRI images from the head to the legs.

Figure 7:
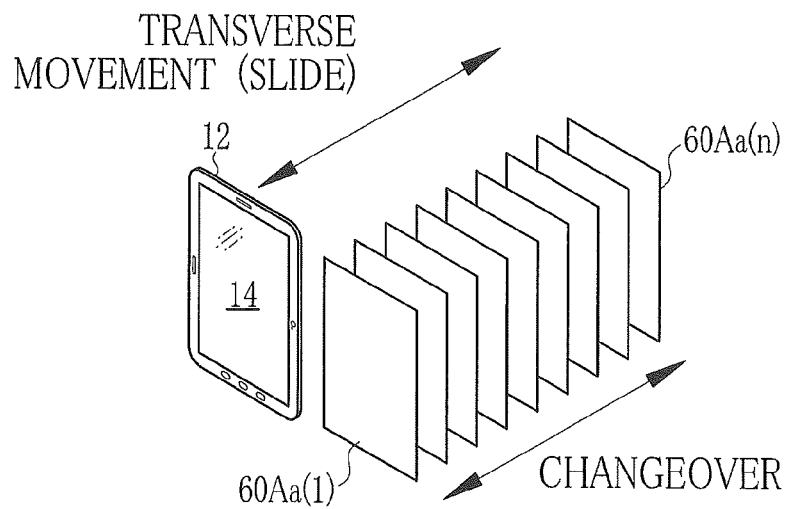
FIG. 7 is an explanatory view illustrating changeover of diagnostic images in a common folder upon a transverse movement of a display unit.

In FIG. 7, the mobile terminal apparatus 12 is transversely moved in the thickness direction in linear movement. In case the mobile terminal apparatus 12 is transversely moved in the backward direction while one of the diagnostic images 60Aa(1)-(n) is displayed on the display unit 14 according to the first date folder 60Aa (formed on 1 Mar. 2012 by the CT imaging of the patient A), then the display image on the display unit 14 is changed over to a succeeding sectional image immediately next to the present sectional image among the diagnostic images 60Aa(1)-(n) upon each shift of a transverse movement (slide) of a predetermined distance, for example, 1 cm. In case the mobile terminal apparatus 12 is transversely moved in the forward direction while one of the diagnostic images 60Aa(1)-(n) is displayed on the display unit 14, then the display image on the display unit 14 is changed over to a preceding sectional image immediately short of the present sectional image among the diagnostic images 60Aa(1)-(n) upon each shift of a transverse movement of a predetermined distance, for example, 1 cm.

Similarly, in case the mobile terminal apparatus 12 is transversely moved in the forward or backward direction while one of the diagnostic images 60Ab(1)-(n) is displayed on the display unit 14, then the display image on the display unit 14 is changed over within the second date folder 60Ab upon each shift of the transverse movement. In case the mobile terminal apparatus 12 is transversely moved in the forward or backward direction while one of the diagnostic images 60Ba(1)-(n) is displayed on the display unit 14, then the display image on the display unit 14 is changed over within the third date folder 60Ba upon each shift of the transverse movement. It is possible to change over the display image in relation to the date folders 60Aa, 60Ab and 60Ba as subfolders by transversely moving the mobile terminal apparatus 12 forwards or backwards.

In FIG. 8, in case the mobile terminal apparatus 12 is shaken by a single shake while one of the diagnostic images 60Aa(1)-(n) is displayed on the display unit 14 according to the first date folder 60Aa (formed on 1 March 2012 by the CT imaging of the patient A), then the display image on the display unit 14 is changed over to one of the diagnostic images 60Ab(1)-(n) according to the second date folder 60Ab (formed on 1 Mar. 2013 by the CT imaging of the patient A) upon each time of a single shake of the mobile terminal apparatus 12.

In case the mobile terminal apparatus 12 is shaken by a single shake while one of the diagnostic images 60Ab(1)-(n) is displayed on the display unit 14 according to the second date folder 60Ab, then the display image on the display unit 14 is changed over to one of the diagnostic images 60Aa(1)-(n) according to the first date folder 60Aa (for example, the first diagnostic image 60Ab(1)) upon each time of a single shake of the mobile terminal apparatus 12. Note that only the third date folder 60Ba (formed on 1 Feb. 2013) is stored in the MRI imaging folder 60B (MRI imaging of the patient A). There is no changeover of a diagnostic image even upon a single shake of the mobile terminal apparatus 12 while the one of the diagnostic images 60Ba(1)-(n) is displayed on the display unit 14.

As illustrated in FIG. 9, in case the mobile terminal apparatus 12 is shaken in a manner of a double shake while one of the diagnostic images 60Aa(1)-(n) and 60Ab(1)-(n) of the CT imaging folder 60A (CT imaging of the patient A) is displayed on the display unit 14, then the display image on the display unit 14 is changed over to one of the diagnostic images 60Ba(1)-(n) in the MRI imaging folder 60B (MRI imaging of the patient A), for example, the first diagnostic image 60Ba(1).

Similarly, in case the mobile terminal apparatus 12 is shaken in a manner of a double shake while one of the diagnostic images 60Ba(1)-(n) of the MRI imaging folder 60B is displayed on the display unit 14, then the display image on the display unit 14 is changed over to one of the diagnostic images 60Aa(1)-(n), for example, the first diagnostic image 60Aa(1), or to one of the diagnostic images 60Ab(1)-(n), for example, the first diagnostic image 60Ab(1). Note that a plurality of folders are provided, such as the date folders 60Aa and 60Ab, and store diagnostic images to be changed over. It is possible according to preference to determine one of the folders of which a diagnostic image will be displayed. It is preferable to change over to a diagnostic image of a folder (the second date folder 60Ab in the embodiment) of which image relevancy is high between states before and after the changeover, for example, according to nearness of their image dates.

As described heretofore, it is possible readily to change over the display of diagnostic images in a common folder and to change over the display of diagnostic images between folders by moving the mobile terminal apparatus 12. The manipulation of the mobile terminal apparatus 12 of the present invention is still easier than a structure in which an input panel is operated for changing over the display.

The details of the structure of the invention are not limited to the above embodiments and can be constructed with degree of freedom for the purpose of display changeover of a diagnostic image in a common folder and between folders by motion of a mobile terminal apparatus. For example, diagnostic images are sectional images (CT or MRI images). However, diagnostic images of the invention can be images other than sectional images.

Diagnostic images can be formed by any known imaging modality, for example, can be an X-ray image, ultrasound echo image, endoscopic image, electrocardiogram data, and data of other graphs.

In the above embodiments, the mobile terminal apparatus is moved in the motion modes for display changeover in a folder, for display changeover between folders, and for display changeover between folders of different tree levels. However, types of the motion modes of the mobile terminal apparatus and associated display changeover operations can be determined according to requirements. For example, the mobile terminal apparatus can be moved in two motion modes for two display changeover operations, and can be moved in four motion modes for four display changeover operations.

Furthermore, motion modes of the mobile terminal apparatus and types of the display changeover can be combined with one another without limitation to the above examples. For example, a single shake can be carried out for the display changeover in a folder. A double shake can be carried out for the display changeover between folders. Also, a transverse movement can be carried out for the display changeover between folders. Also, a rotational movement of the mobile terminal apparatus can be utilized for the display changeover in a folder or the display changeover between folders. Examples of the rotational movement are rotation with 90 degrees from the vertical orientation to the horizontal orientation, and rotation with 90 degrees from the horizontal orientation to the vertical orientation.

Note that the motion mode of the mobile terminal apparatus for display changeover in the folder is not limited to one motion mode. A first motion mode can be predetermined as any one of plural simple motion modes. For example, the changeover in the folder is carried out upon occurrence of at least one of a transverse movement and a shake. Also, a second motion mode and a third motion mode can be predetermined as any one of plural simple motion modes for the purpose of display changeover in the folder.

In the above embodiments, the lowest-level subfolders are the date folders at a lower tree level than the imaging folders. The parent folder at a highest tree level is the patient folder. However, a hierarchical tree structure for various diagnostic images can be determined suitably in a multi-level form. The number of the tree levels of the folders is not limited to three but can be two, four or more. Types of folders are not limited. For example, folders can be a condition folder of which diagnostic images are obtained in the same condition, and a body part folder of which diagnostic images are obtained from the same body part. Furthermore, it is possible for a user manually to input information to establish and modify a hierarchical tree structure for use in the present invention.

It is conceivable to change over the display between the patient folders according to the motion mode of the mobile terminal apparatus, for example, by shaking the mobile terminal apparatus to change over a diagnostic image in the folder of the patient A to a diagnostic image in the folder of the patient B. However, a problem may arise in that the mobile terminal apparatus is moved incidentally without attention of a user. A diagnostic image of a wrong patient may appear and may be diagnosed improperly for the purpose. Therefore, it is preferable to display message information on the display for confirmation before display changeover between the folders of the patients, and to change over the display only in case the user confirms the message.

It is possible in view of the purpose to determine which of the folders should be selected for designating a diagnostic image as a display image for the purpose of display changeover from a first folder containing the display image to a second folder containing a second diagnostic image. However, a problem may arise in a low relevancy between states before and after the changeover. For example, the diagnostic image 60Aa(n) of FIG. 6 is disposed in the sequence as a large sequence number (side of the legs). The diagnostic image 60Ab(1) is disposed in the sequence as a small sequence number (side of the head). The changeover is carried out from the diagnostic image 60Aa(n) to the diagnostic image 60Ab(1). There is a difference in the body part between the diagnostic images to lower the relevancy between the diagnostic images. Their comparison becomes difficult.

Thus, it is preferable to determine a diagnostic image to be changed over to set body parts near to one another between the states before and after the changeover in view of changeover between the plural folders. For example, it is possible to change over the display to a diagnostic image of the same sequence number as a diagnostic image before the changeover. Furthermore, it is possible to determine a sequence of diagnostic images by setting values of a sequence ratio the nearest to one another before and after the changeover, the sequence ratio being a proportion of the sequence number of a diagnostic image to a total number of diagnostic images in the folder.

Note that it is likely that there is no relevancy between two folders with diagnostic images before and after the changeover. For example, a first folder contains CT images of the head. A second folder contains X-ray images of the legs. It is meaningless to determine a diagnostic image to be displayed after the changeover even in considering the sequence number of the image, sequence ratio, and other values.

It is possible to check relevancy between diagnostic images stored in the folders before and after the changeover, for example, in relation to a body part of the imaging and imaging modality. Only in case there is sufficiently high relevancy, it is possible to determine a diagnostic image to be displayed after the changeover by considering the sequence of diagnostic images in the folder and a sequence ratio of the sequence number to a total number of the diagnostic images in the folder. To evaluate the relevancy between diagnostic images, it is possible to utilize attribute information such as a folder name of an image folder or a higher-level parent folder, imaging condition assigned to the diagnostic image upon the imaging, and the like. Also, a diagnostic image can be analyzed so as to evaluate the relevancy according to a result of the analysis.

Note that transversely moving the mobile terminal apparatus of the horizontal orientation in the forward direction means the same as moving up the same. Transversely moving the mobile terminal apparatus of the horizontal orientation in the backward direction means the same as moving down the same. Transversely moving the mobile terminal apparatus of the vertical orientation in the forward direction means the same as horizontally advancing the same. Transversely moving the mobile terminal apparatus of the vertical orientation in the backward direction means the same as horizontally retracting the same. It is possible by use of the motion modes to change over the display image to view body parts in a depth direction in the patient's subject body.

For this structure, a first motion mode is a transverse movement of the mobile terminal apparatus in the forward or backward direction (thickness direction in linear movement). A second motion mode is a rotational motion of the mobile terminal apparatus, either from the horizontal orientation to the vertical orientation or from the vertical orientation to the horizontal orientation.

As illustrated in FIG. 10, a patient folder 70 as a parent directory (data group) of the patient A stores a CT imaging folder 70A as a directory. A horizontal image folder 70Aa as an image group (subdirectory) and a vertical image folder 70Ab as an image group (subdirectory) are stored in the CT imaging folder 70A. Also, diagnostic images 70Aa(1)-(n) are stored in the horizontal image folder 70Aa as axial slice images of the patient's head from horizontal planes that are perpendicular to a body axis of the subject body, and in a sequence from a top of the head to the neck. Diagnostic images 70Ab(1)-(n) are stored in the vertical image folder 70Ab as coronal slice images of the patient's head from vertical planes that are parallel to a forehead of the subject body, and in a sequence from the nose to the back of the head.

Figure 11:
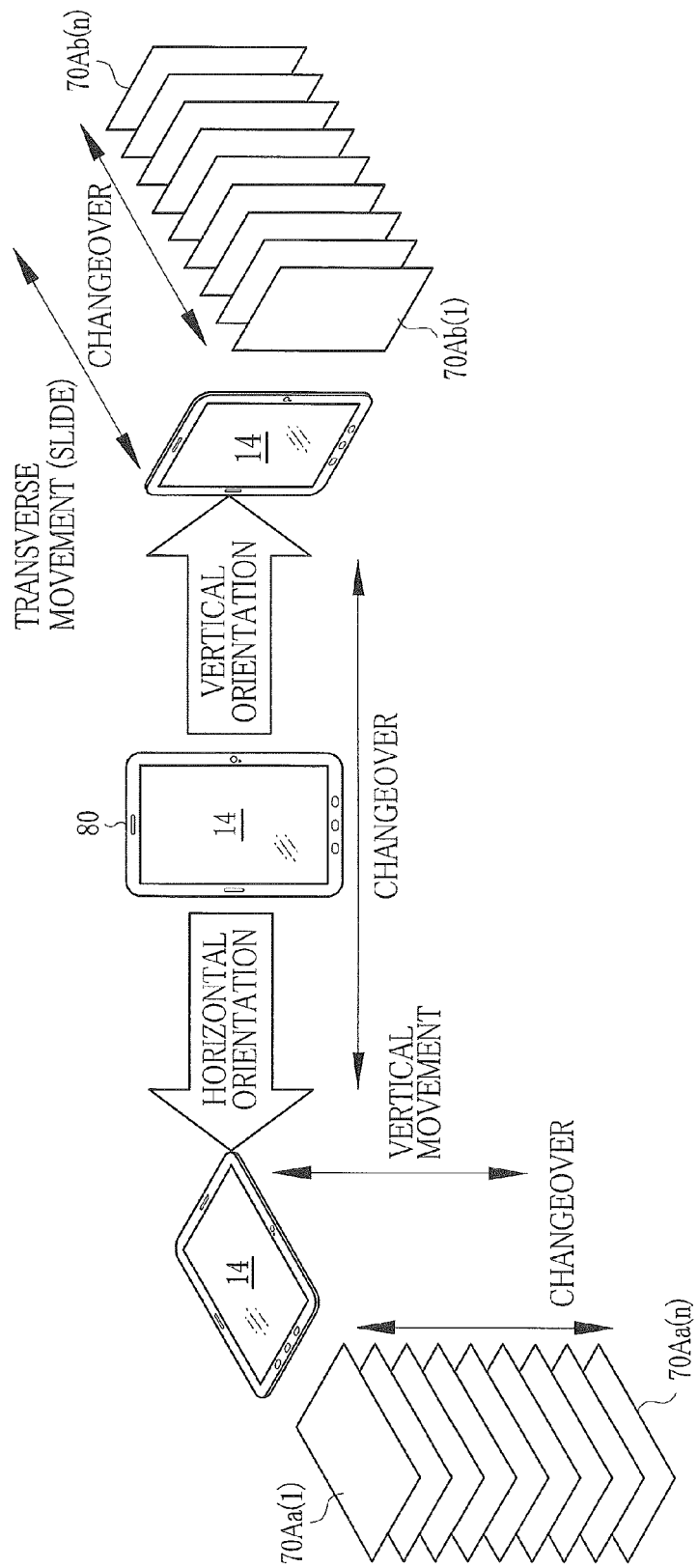
FIG. 11 is an explanatory view illustrating another preferred embodiment of changeover of diagnostic images upon a transverse movement and rotational movement.

In case a mobile terminal apparatus 80 is oriented in a horizontal orientation as illustrated in FIG. 11, any one of the diagnostic images 70Aa(1)-(n) in the horizontal image folder 70Aa is displayed. In case the mobile terminal apparatus 80 in this state is moved in the backward direction (moved down), the display is changed over to a diagnostic image succeeding to the display image at each time of a predetermined shift. In case the mobile terminal apparatus 80 in this state is moved in the forward direction (moved up), the display is changed over to a diagnostic image preceding to the display image at each time of a predetermined shift.

In case the mobile terminal apparatus 80 is oriented vertically, one of the diagnostic images 70Ab(1)-(n) in the vertical image folder 70Ab for the vertical section is displayed. Assuming that the mobile terminal apparatus 80 is moved backwards, the sectional image (coronal) is changed over to a second sectional image (side of the back of the head) succeeding to the sectional image at each time of a predetermined shift. Assuming that the mobile terminal apparatus 80 is moved forwards, the sectional image is changed over to a second sectional image (side of the nose) preceding to the sectional image at each time of a predetermined shift.

In case the mobile terminal apparatus 80 is oriented horizontally, a sectional image of a horizontal section is displayed. Assuming that the mobile terminal apparatus 80 is moved upwards, the sectional image is changed over to a second sectional image with a body part of a higher position than the sectional image. Assuming that the mobile terminal apparatus 80 is moved downwards, the sectional image is changed over to a second sectional image with a body part of a lower position than the sectional image. In case the mobile terminal apparatus 80 is oriented vertically, a sectional image (coronal) of a vertical section is displayed. Assuming that the mobile terminal apparatus 80 is moved forwards, the sectional image is changed over to a second sectional image with a body part of a front position (side of the nose) from the sectional image. Assuming that the mobile terminal apparatus 80 is moved backwards, the sectional image is changed over to a second sectional image with a body part of a rear position (side of the back of the head) from the sectional image. Thus, it is possible to view sectional images not only in a two-dimensional manner but in a depth direction in the patient's subject body.

Also, the feature of the construction of FIGS. 10 and 11 can be used for a folder for coronal slice images and a folder for sagittal slice images. The coronal slice images are images of a vertical section on a plane parallel to a forehead of a patient. The sagittal slice images are images of a vertical section on a plane that is perpendicular to the forehead and perpendicular to a horizontal plane. In case the mobile terminal apparatus 12 is rotationally moved from the vertical orientation to a second vertical orientation with 90 degrees, the display image can be changed over between the coronal and sagittal slice images.

In the above embodiments, plural diagnostic images are downloaded from the server apparatus in the unit of a folder. However, only one diagnostic image can be downloaded (without a folder) to display a diagnostic image or change over a display image for the purpose of initial display or changeover of the display.

Furthermore, the use of the folder of diagnostic images may be omitted. In short, diagnostic images can be grouped not with folders but with image groups. An image group of plural diagnostic images is stored directly in a parent folder at a higher tree level. In case the mobile terminal apparatus is moved in a first motion mode, diagnostic images are changed over within the image group. In case the mobile terminal apparatus is moved in a second motion mode, diagnostic images are changed over between image groups.

The image groups can be defined by grouping diagnostic images in a method other than forming the image folders or directories. For example, an image list is created in a form of a document file. File names of diagnostic images are designated as links to image data of the diagnostic images, so as to open the diagnostic images in response to clicking the file names. A plurality of such image lists can be defined at plural tree levels to locate the images in consideration of the patients, imaging modalities and image dates of the diagnostic images.

Also, the image storage device 44 is incorporated in the mobile terminal apparatus 12, but can be a removable storage medium, for example, a USB memory stick, flexible disk, CD and the like.

The feature of the present invention can be used not only for the apparatus and system but for a computer-executable program and a storage medium for storing the same.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A mobile terminal apparatus comprising:
   an image storage device for storing at least first and second image groups, each of said first and second image groups including a plurality of diagnostic images;
   a display unit for displaying one of said diagnostic images read from said image storage device;
   an orientation sensor for detecting first and second motion modes of said display unit with a difference in movement from one another; and
   a display control unit for display control of said display unit by sending an image signal thereto, and for changing over said image signal according to an output of said orientation sensor,
   wherein assuming that said display unit is moved in said first motion mode while a first diagnostic image included in said first image group is displayed on said display unit, then said display control unit carries out changeover to display a second diagnostic image being included in said first image group and different from said first diagnostic image, and assuming that said display unit is moved in said second motion mode while said first diagnostic image is displayed on said display unit, then said display control unit carries out changeover to display a third diagnostic image included in said second image group.

2. A mobile terminal apparatus as defined in claim 1, further comprising a terminal housing for containing said display unit.

3. A mobile terminal apparatus as defined in claim 1, further comprising:
   a communication interface for connection to a server apparatus by communication network connection; and
   a controller for acquiring said diagnostic images from said server apparatus through said communication interface, and storing said diagnostic images to said image storage device.

4. A mobile terminal apparatus as defined in claim 1, wherein said first motion mode comprises to move said display unit linearly.

5. A mobile terminal apparatus as defined in claim 4, wherein each of said image groups is defined by arranging said diagnostic images in a predetermined sequence; and
   while said display unit is moved linearly in a thickness direction, said diagnostic images are serially changed over according to said sequence to be displayed on said display unit at each time of linear movement in said thickness direction at a predetermined amount.

6. A mobile terminal apparatus as defined in claim 4, wherein said second motion mode comprises to shake said display unit.

7. A mobile terminal apparatus as defined in claim 6, wherein said second motion mode comprises to shake said display unit two times.

8. A mobile terminal apparatus as defined in claim 4, wherein said second motion mode comprises to move said display unit rotationally between a horizontal orientation in which a display surface is horizontally extended and a vertical orientation in which said display surface is vertically extended.

9. A mobile terminal apparatus as defined in claim 8, wherein said first image group has diagnostic images for display in said horizontal orientation, and said second image group has diagnostic images for display in said vertical orientation, and
wherein said display control unit causes said display unit to display one of said diagnostic images of said first image group in a case of said horizontal orientation, and to display one of said diagnostic images of said second image group in a case of said vertical orientation.

10. A mobile terminal apparatus as defined in claim 4, wherein said second motion mode comprises to rotate said display unit about an axis extending vertically in a vertical orientation in which a display surface of said display unit is vertically extended.

11. A mobile terminal apparatus as defined in claim 10, wherein:
said first image group has a sagittal slice image for said diagnostic images, and said second image group has a coronal slice image for said diagnostic images;
said vertical orientation includes a first vertical orientation extending along a sagittal plane, and a second vertical orientation extending along a coronal plane being perpendicular to a horizontal surface and said sagittal plane; and
said display control unit causes said display unit to display said sagittal slice image of said first image group in a case of said first vertical orientation, and to display said coronal slice image of said second image group in a case of said second vertical orientation.

12. A mobile terminal apparatus as defined in claim 1, wherein said image storage device stores plural data groups of a higher level, each of said data groups having said first and second image groups, and
wherein, assuming that said display unit is moved in a third motion mode different from said first and second motion modes while said first diagnostic image is displayed on said display unit, then said display control unit carries out changeover to display a fourth diagnostic image included in one of said data groups different from a data group of said first diagnostic image.

13. A mobile terminal apparatus as defined in claim 12, wherein assuming that said display unit is moved in said third motion mode while said first diagnostic image is displayed on said display unit, then said display control unit outputs message information to said display unit for possibility of changeover;
said mobile terminal further comprising an input interface, externally operable, for inputting a signal for allowing said changeover to said fourth diagnostic image, to change over said display unit with said display control unit.

14. A mobile terminal apparatus as defined in claim 13, wherein a subject body in said diagnostic image is different between said plural data groups.

15. The mobile terminal apparatus as defined in claim 12, wherein said first and second diagnostic images are contained in a first folder, said third diagnostic image is contained in a second folder, and said fourth diagnostic image is contained in a third folder.

16. The mobile terminal apparatus as defined in claim 15, wherein said first and second folders comprise child folders of a first parent folder, and said third folder comprises a child folder of a second parent folder that is different from said first parent folder but is at the same tree level of said first parent folder.

17. A mobile terminal apparatus as defined in claim 1, wherein said diagnostic images comprise a sectional image of a subject body, and each of said first and second image groups is formed at one time of imaging of said subject body.

18. A mobile terminal apparatus as defined in claim 17, wherein said sectional image comprises a CT or MRI image.

19. A mobile terminal apparatus as defined in claim 1, wherein said first image group includes diagnostic images of a first imaging modality, and said second image group includes diagnostic images of a second imaging modality different from said first imaging modality.

20. A mobile terminal apparatus as defined in claim 1, wherein said first image group includes diagnostic images with first image date information, and said second image group includes diagnostic images with second image date information different from said first image date information.

21. A mobile terminal apparatus as defined in claim 1, wherein said image storage device stores:
first and second directories adapted to store diagnostic images of imaging modalities different from one another; and
first and second subdirectories, located in at least one of said first and second directories, for storing diagnostic images with image date information different from one another,
wherein said first image group comprises said first directory or said first subdirectory, and said second image group comprises said second directory or said second subdirectory.

22. The mobile terminal apparatus as defined in claim 1, wherein said first and second diagnostic images are contained in a first folder and said third diagnostic image is contained in a second folder.

* * * * *